US00PP23407P3

(12) United States Plant Patent
Philley et al.

(10) Patent No.: US PP23,407 P3
(45) Date of Patent: Feb. 19, 2013

(54) BERMUDAGRASS PLANT NAMED 'MSB-04-264'

(50) Latin Name: ***Cynodon dactylon*×*C. transvaalensis***
Varietal Denomination: MSB-04-264

(75) Inventors: H. Wayne Philley, Mathiston, MS (US); Gregg C. Munshaw, Starkville, MS (US)

(73) Assignee: Mississippi State University, Mississippi, MS (US)

( * ) Notice: Subject to any disclaimer, the term of this patent is extended or adjusted under 35 U.S.C. 154(b) by 0 days.

(21) Appl. No.: 13/065,578

(22) Filed: Mar. 24, 2011

(65) Prior Publication Data

US 2011/0239341 P1 Sep. 29, 2011

Related U.S. Application Data

(60) Provisional application No. 61/340,915, filed on Mar. 24, 2010.

(51) Int. Cl.
*A01H 5/00* (2006.01)

(52) U.S. Cl. ..... Plt./389

(58) Field of Classification Search ..... Plt./389
See application file for complete search history.

*Primary Examiner* — Annette Para
(74) *Attorney, Agent, or Firm* — Lawrence Arthur Schemmel

(57) ABSTRACT

Bermudagrass plant 'MSB-04-264' is a new and distinct variety of bermudagrass cultivar characterized by its good growth habit, extremely fine leaf texture, upright as opposed to prostrate leaf orientation, and good fall and winter color retention. 'MSB-04-264' is particularly suited for golf course greens and the like.

5 Drawing Sheets

STATEMENT OF GOVERNMENT SUPPORT

This invention was made with government support under 0209438 awarded by the Cooperative State Research, Education, and Extension Service, USDA. The government may have certain rights in the invention.

Latin name: *Cynodon dactylon*×*C. transvaalensis*.
Varietal denomination: 'MSB-04-264'.

BACKGROUND OF THE INVENTION

The present invention relates to the field of plants and more specifically to the field of bermudagrass plants and involves a new and distinct cultivar of bermudagrass plant, botanically known as *Cynodon dactylon*×*C. transvaalensis* and referred to hereinafter by its varietal denomination 'MSB-04-264'. This novel triploid hybrid bermudagrass cultivar originated from planned hybridization at Starkville, Miss. in 2003. It has superior growth habits, color, and fall color retention and is particularly adaptable to golf course greens.

Asexual reproduction of the new turfgrass cultivar 'MSB-04-264' by vegetative propagation was directed by the inventors and has shown that the unique traits, features, and characteristics of this novel plant as described have in fact been maintained, are stable, and have been reproduced true-to-type in several successive generations. This novel and distinct variety of bermudagrass plant was asexually reproduced at Starkville, Miss.

SUMMARY OF THE INVENTION

The cultivar 'MSB-04-264' is a distinctive new variety of bermudagrass plant characterized by good growth habit, extremely fine leaf texture, upright as opposed to prostrate leaf orientation, and good fall and winter color retention and is particularly suited for golf course greens and the like.

DETAILED BOTANICAL DESCRIPTION OF THE VARIETY

Figure 1A:
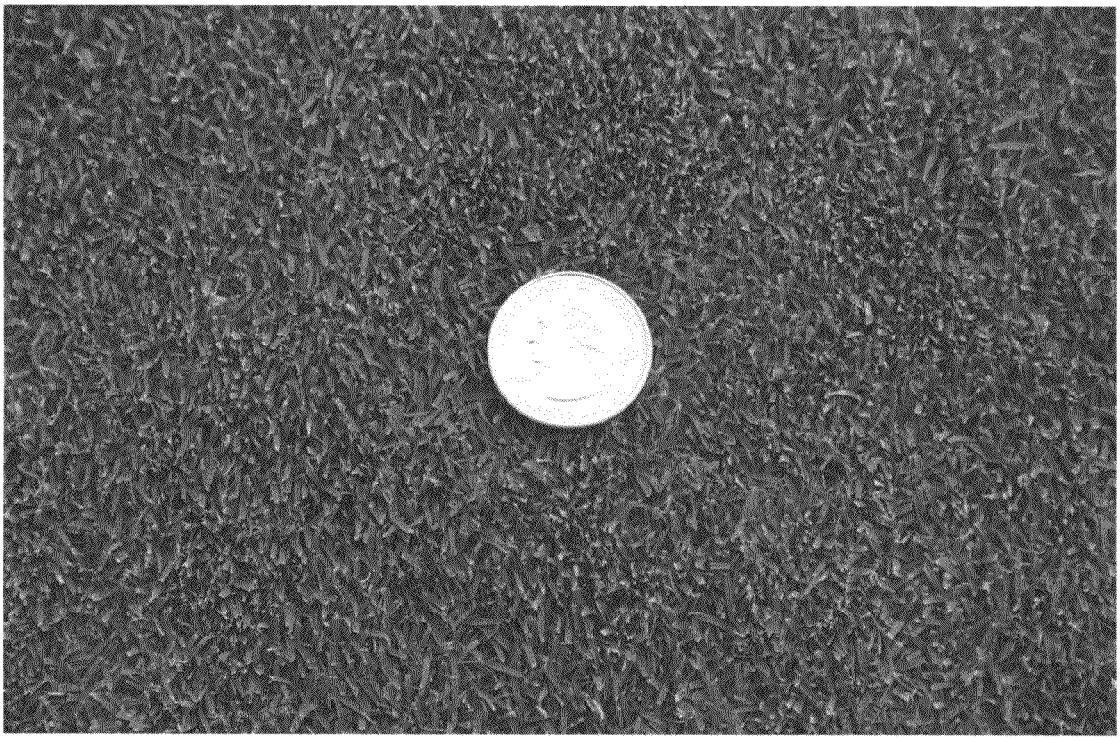
FIG. 1A is a photograph of the new cultivar and illustrates the fine leaf texture and upright leaf orientation of 'MSB-04-264'. The photograph also shows that many of the leaf tips or blades are clipped when mowed.

Latin name: *Cynodon dactylon*×*Cynodon transvaalensis*.
Variety denomination: 'MSB-04-264'.

The present invention is a new and distinct *Cynodon dactylon*×*Cynodon transvaalensis* cultivar known as 'MSB-04-264' that is different from and morphologically advantageous compared to other bermudagrass cultivars. The following is a detailed botanical description of the characteristics of the new 'MSB-04-264' bermudagrass cultivar, based upon observations of the plant grown under natural conditions in Oktibbeha County, Miss.

Color notations of plant tissues are based upon the Munsell® Color Chart for plant tissues [Munsell Book of Color: Glossy Finish Edition, Munsell Color, Baltimore, Md., 1976; and Munsell Color Charts for Plant Tissues, Munsell Color, Baltimore, Md., 1977]. Color notations are affected by light quality and fertility and general plant growth. Certain characteristics of the new plant may vary depending on the age of the plant, such that characteristics such as dimensions, sizes, and/or colors are approximations or averages since the variety has not been observed under every possible environmental condition. Therefore, as will be apparent to those skilled in horticultural science, the phenotype of the novel variety may differ from the descriptions depending upon environmental variations including, but not limited to, the season, climate, soil, temperatures, day lengths, light direction and quality, and fertilization, as well as other factors. The photographs and the detailed description of the invention are intended to illustrate further the invention and its advantages.

Introduction

Bermudagrass cultivars that are currently used on closely-mowed golf putting greens all originated after somatic mutation in previously-used cultivars. 'Tifgreen' bermudagrass (experimental designation 328), released from an experiment station at Tifton, Ga. in 1956, resulted from interspecific hybridization of selections of common bermudagrass (*Cynodon dactylon*) and African bermudagrass (*Cynodon transvaalensis*). 'Tifgreen' bermudagrass was widely used across the southern United States for several years until golf course management moved to lower mowing heights that were beyond its limit of performance. 'Tifgreen' is a sterile triploid (2n=3X=36) hybrid that produces no seed. Most of the dwarf and ultradwarf bermudagrasses used on putting greens today descended from 'Tifgreen' by vegetative propagation of selected naturally occurring mutants. 'Tifdwarf', 'MS-Supreme' (U.S. Plant Pat. No. 11,781), and 'Floradwarf' (U.S. Plant Pat. No. 9,030) were recovered directly from 'Tifgreen'. 'Champion' (U.S. Plant Pat. No. 9,888) and 'Mini-Verde' (U.S. Plant Pat. No. 12,084) were selected from 'Tifdwarf'. One exception, 'TifEagle' (U.S. Plant Pat. No. 11,163), an induced mutant, was selected from stolons of a taller cultivar, 'Tifway II', that had been exposed to gamma radiation.

Ultradwarf bermudagrasses are tolerant of frequent mowing at very low cutting heights (<0.188 inches). The short-bladed leaves of these cultivars lie close and parallel to the soil surface and therefore many avoid being clipped by a mower. The prostrate leaf orientation of existing ultradwarf bermudagrass cultivars also results in grain on the putting surface of a golf green that can be objectionable to golfers. The putting surface can be so firm that golf shots often will roll completely off a green.

'MSB-04-264' is a new bermudagrass cultivar that comes from a much different genetic background with no mutations involved. The leaf texture of 'MSB-04-264' under close mowing is extremely fine. The leaf orientation is more upright than ultradwarf cultivars. The growth habit is more similar to that of creeping bentgrass (*Agrostis stolonifera*), a species preferred by most golfers that provides a highly-desirable golf putting surface in cooler climates. Due to this advantageous growth habit, the new cultivar 'MSB-04-264' has the potential to allow truer putting and to hold golf shots better than existing ultradwarf bermudagrass cultivars.

Origin

'MSB-04-264' originated from planned hybridization at Starkville, Miss. in 2003. The seed (female) parent, an experimental genotype labeled 'MSB 28-18', is a very fine-leafed low-growing tetraploid (2n=4x=36) selection of *Cynodon dactylon*. The pollen (male) parent, an experimental bermudagrass genotype labeled 'trans1', is a selection of *Cynodon transvaalensis*. Cross pollination in May, 2003 of these two plants yielded interspecific sterile hybrids that are triploid. Seeds from this cross pollination were germinated in January, 2004 in a controlled-temperature chamber. The seedlings were then individually transplanted to greenhouse pots. 'MSB-04-264' originated from a single seed labeled 28-18 x trans1-2 and has been vegetatively propagated since germination. In August, 2004 this pot was transplanted to a field nursery into plot number 264. Other promising plants resulted from the same cross and were evaluated at the same time, including a full sibling, 'MSB-04-265', and half siblings, 'MSB-04-268' and 'MSB-04-271'.

Turf Performance

University Golf Course

To compare 'MSB-04-264' to six (6) other bermudagrasses under a putting green culture, a short duration micro-plot trial was established at a university golf course at Starkville, Miss. in August, 2006. A fully-established, well-maintained, and actively-used putting surface of 'MS-Supreme' bermudagrass was chosen for the test site. Holes were dug of out of the green in straight lines on three-foot centers for each of the seven (7) trial bermudagrass cultivars (Table 1). One six-inch diameter pot of greenhouse-grown test bermudagrass of each of the seven cultivars was transplanted to its own respective hole and carefully leveled by backfilling with sand to grade to restore the surface. The experiment was laid out in a randomized complete block design with three (3) replications of each cultivar. The entire green was mowed daily at 0.125 inches height.

Figure 1B:
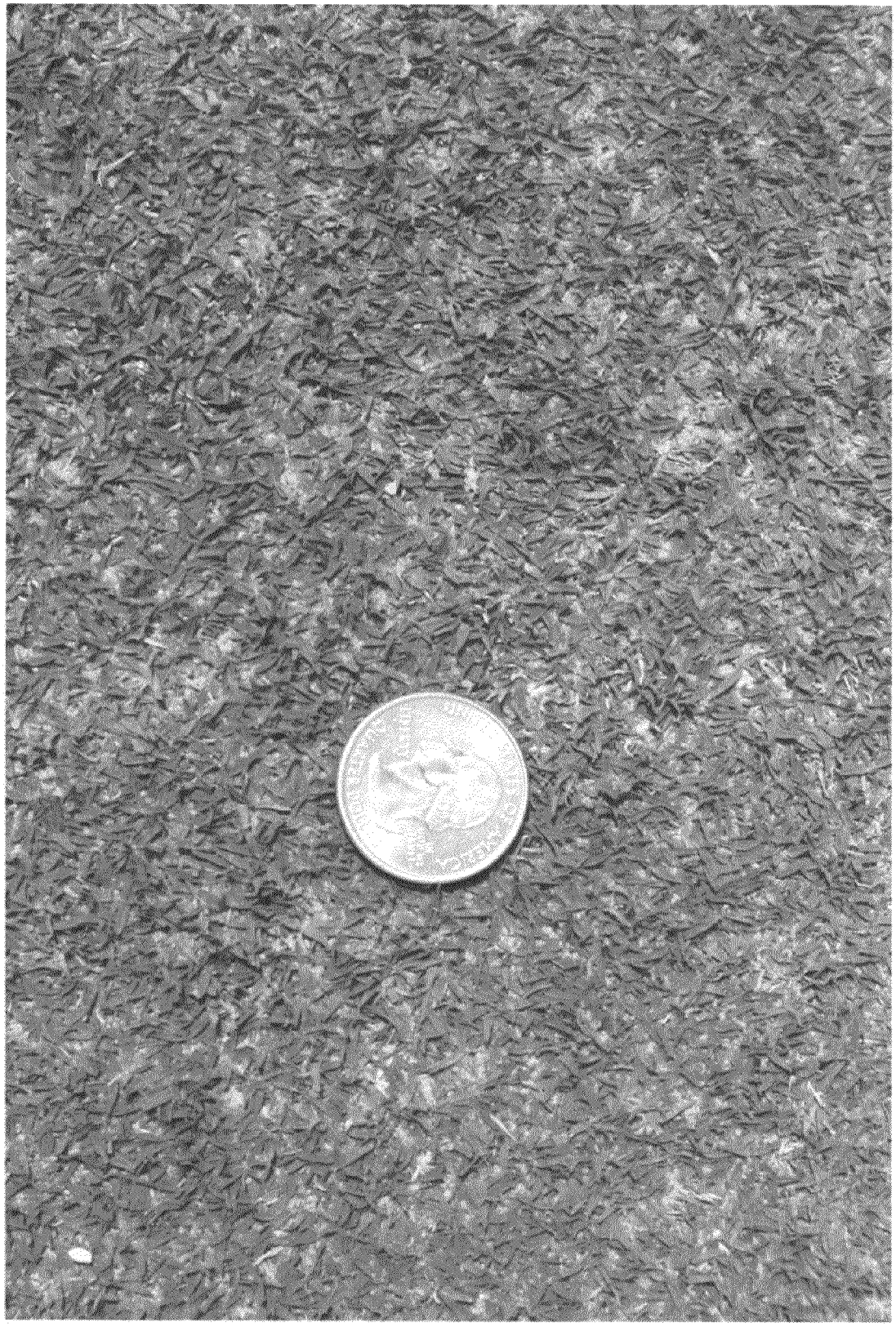
FIG. 1B is a photograph of the prostrate leaf orientation of 'Champion' bermudagrass and shows that significantly less leaf tips or blades of 'Champion' are clipped by a mower than those of 'MSB-04-264' bermudagrass (FIG. 1A). The photograph also shows that most leaves of 'Champion' still have their tips after being mowed (i.e., were not clipped) compared to the leaves of 'MSB-04-264', which did not have their tips after being mowed (i.e., were clipped).

Visual ratings of leaf texture (Table 1) at the university golf course revealed that 'MSB-04-264' produced very fine leaves at low mowing height. When averaged across three dates of ratings, the leaf texture of 'MSB-04-264' was extremely fine and received the highest rating of all the cultivars tested. The leaf texture of 'MSB-04-264' was significantly finer than the popular commercial cultivars 'Champion', 'TifEagle', and 'Tifdwarf' (FIGS. 1A and 1B). Turf density was rated twice during this evaluation (Table 2). The turf density of 'MSB-04-264' was significantly higher than 'Champion', 'TifEagle', and 'Tifdwarf' on both dates of rating. High density and fine leaf texture are very desirable traits for a golf green putting surface, making 'MSB-04-264' an excellent choice for such application.

Figure 2:
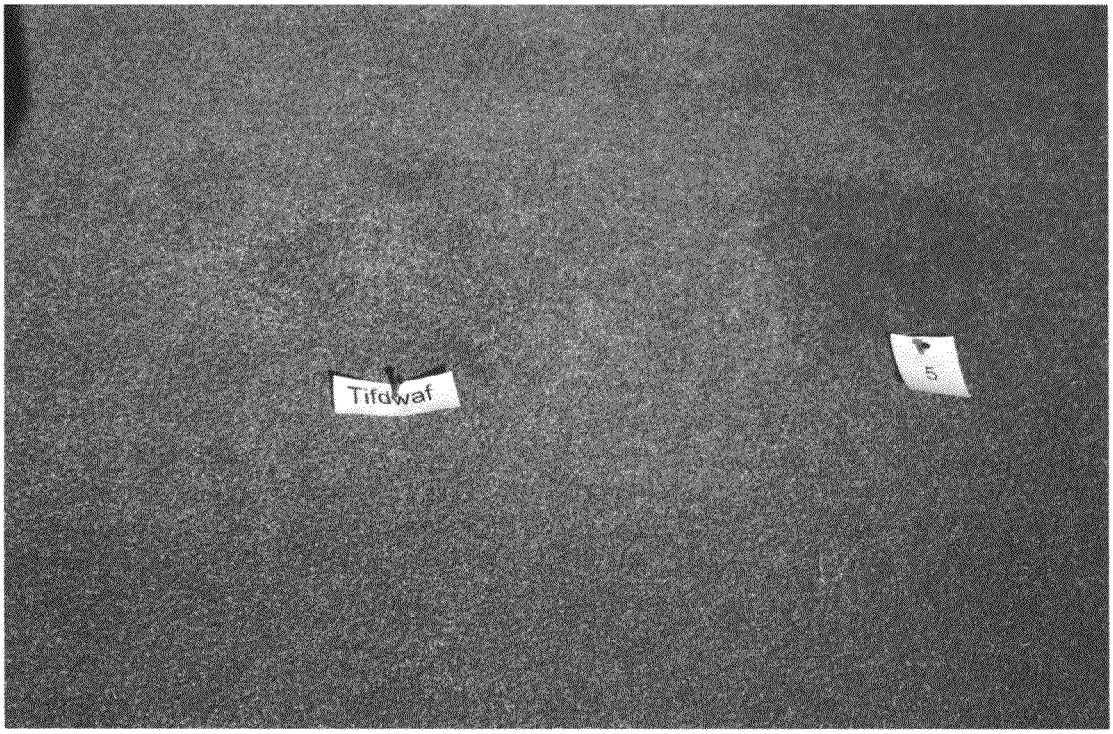
FIG. 2 is a photograph of the new cultivar taken on Nov. 3, 2006 at the university golf course at Starkville, Miss., and illustrates the fall color retention of 'MSB-04-264' labeled as entry #5 in the micro-plot on the right, as compared to 'Tifdwarf' in the micro-plot on the left.

Fall color retention ratings are typically used to assess the ability of a grass to hold color during the changing climatic conditions of fall, including chilling, frost, and shorter days and daylight hours. 'MSB-04-264' retained significantly more green color throughout fall than 'Champion', 'TifEagle', and 'Tifdwarf' (Table 3). Bermudagrasses are typically dormant in winter. However, in this test 'MSB-04-264' held some color even in January (Table 3) when 'Champion', 'TifEagle', and 'Tifdwarf' were completely dormant (FIG. 2). This trait of 'MSB-04-264' could be very desirable in areas where winters are mild and temperatures are less often below freezing.

Plant Science Research Center

A larger plot trial was established in Fall, 2008 at a plant science research center at Starkville, Miss. on a sand-based research green. Seven (7) bermudagrass cultivars were planted, each into its own 9 foot×10 foot plots by placing seventy-two (72) 2-inch diameter plugs on one-foot centers. The layout for this trial was a randomized complete block with two replications. These plots grew and established during the spring and summer of 2009 and were mowed five (5) times per week at 0.125 inches height.

Leaf texture was rated in July, 2009 and August, 2010 (Table 4). 'MSB-04-264' leaf texture was extremely fine and again received the finest texture rating of all the cultivars tested. The rating for 'MSB-04-264' was significantly finer than 'Tifdwarf', and finer though not significantly than 'Champion' and 'TifEagle'.

Figure 3:
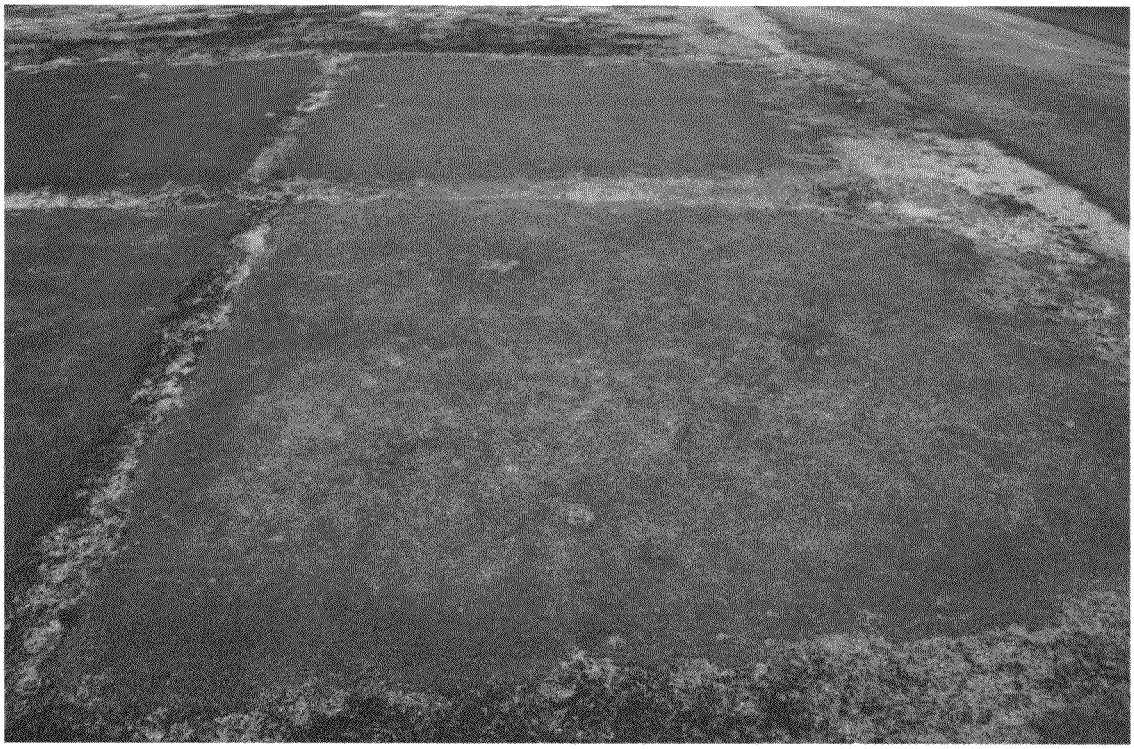
FIG. 3 is a photograph of the new cultivar taken on Nov. 17, 2009 at a research center at Starkville, Miss. and illustrates the fall color retention of 'MSB-04-264'. 'Champion' bermudagrass is shown in the foreground and 'MSB-04-264' is shown displaying significantly more color in the background located immediately behind the 'Champion' bermudagrass plot.

Genetic color ratings are typically conducted when turf is actively growing and is not under stress and when the turf reflects the inherent color of the turfgrass genotype. In a July, 2009 rating, the genetic color of 'MSB-04-264' was slightly but not significantly lighter than 'Champion' and 'TifEagle' (Table 4). When rated for fall color retention, however, 'MSB-04-264' held significantly more color than 'TifEagle' on five of the six rating dates (Table 5). The color retention of 'MSB-04-264' was significantly greater than 'Champion' and 'Tifdwarf' on all six rating dates (FIG. 3).

TABLE 1

Leaf texture ratings of bermudagrass cultivars evaluated at a university golf course at Starkville, MS in 2006. (9 = very fine; 1 = course)

| Cultivar | Aug. 29, 2006 | Sep. 22, 2006 | Oct. 17, 2006 | mean |
|---|---|---|---|---|
| 'MSB-04-264' | 7.7 | 7.3 | 8.0 | 7.7 |
| 'MSB-04-265' | 7.0 | 8.0 | 7.3 | 7.4 |
| 'MSB-05-271' | 6.7 | 7.3 | 7.3 | 7.1 |
| 'MSB-05-268' | 6.3 | 7.7 | 7.3 | 7.1 |
| 'Champion' | 6.0 | 7.0 | 6.7 | 6.6 |
| 'Tifdwarf' | 6.0 | 6.3 | 6.7 | 6.3 |
| 'TifEagle' | 5.7 | 6.0 | 6.0 | 5.9 |
| LSD(0.05) | 0.7 | 0.8 | 0.9 | 0.6 |

TABLE 2

Density ratings of bermudagrass cultivars evaluated at a university golf course at Starkville, MS. (9 = very high; 1 = low)

| Cultivar | Sep. 22, 2006 | May 14, 2007 | mean |
|---|---|---|---|
| 'MSB-04-264' | 8.3 | 8.0 | 8.2 |
| 'MSB-04-265' | 7.7 | 8.0 | 7.8 |
| 'MSB-05-271' | 8.0 | 6.7 | 7.3 |
| 'MSB-05-268' | 7.7 | 5.6 | 6.7 |
| 'Champion' | 6.7 | 6.0 | 6.3 |
| 'Tifdwarf' | 7.0 | 5.7 | 6.3 |
| 'TifEagle' | 7.0 | 5.3 | 6.2 |
| LSD(0.05) | 0.8 | 1.4 | 0.8 |

TABLE 3

Fall and winter color retention ratings of bermudagrass cultivars evaluated at a university golf course at Starkville, MS. (9 = fully green; 1 = straw brown)

| | Fall color retention | | Winter color |
|---|---|---|---|
| Cultivar | Nov. 3, 2006 | Dec. 1, 2009 | Jan. 26, 2007 |
| 'MSB-04-264' | 7.0 | 5.3 | 3.0 |
| 'MSB-05-271' | 6.7 | 5.3 | 4.0 |
| 'MSB-04-265' | 6.3 | 5.3 | 3.7 |
| 'MSB-05-268' | 6.0 | 3.3 | 3.0 |
| 'TifEagle' | 5.0 | 2.7 | 1.0 |
| 'Tifdwarf' | 4.7 | 1.7 | 1.0 |
| 'Champion' | 4.3 | 2.0 | 1.0 |
| LSD(0.05) | 0.8 | 1.5 | 0.4 |

TABLE 4

Leaf texture and genetic color ratings of bermudagrass cultivars evaluated at a plant science research center at Starkville, MS. (Leaf texture: 9 = very fine; 1 = course) (Genetic color: 9 = dark green; 1 = light green)

| | Leaf texture | | Genetic color |
|---|---|---|---|
| Cultivar | Jul. 27, 2009 | Aug. 31, 2010 | Jul. 27, 2009 |
| 'MSB-04-264' | 8.5 | 8.0 | 6.5 |
| 'MSB-04-265' | 8.0 | 8.0 | 7.3 |
| 'Champion' | 8.0 | 7.0 | 7.0 |
| 'TifEagle' | 7.5 | 7.0 | 7.3 |
| 'MSB-05-271' | 6.0 | 7.5 | 6.0 |
| 'MSB-05-268' | 5.5 | 7.0 | 6.3 |
| 'Tifdwarf' | 4.5 | 6.5 | 6.5 |
| LSD(0.05) | 2.4 | 1.0 | NS |

TABLE 5

Fall color retention of bermudagrass cultivars evaluated at a plant science research center at Starkville, MS. (9 = fully green; 1 = straw brown)

| Cultivar | Oct. 30, 2009 | Nov. 09, 2009 | Dec. 01, 2009 | Nov. 12, 2010 | Dec. 03, 2010 | Dec. 16, 2010 |
|---|---|---|---|---|---|---|
| 'MSB-04-264' | 7.0 | 7.0 | 6.5 | 8.0 | 8.0 | 7.0 |
| 'MSB-04-265' | 7.0 | 7.0 | 6.5 | 8.0 | 8.0 | 7.0 |
| 'MSB-05-271' | 7.0 | 6.5 | 6.0 | 6.0 | 7.0 | 5.5 |
| 'MSB-05-268' | 6.0 | 5.0 | 4.0 | 6.0 | 7.0 | 6.0 |
| 'TifEagle' | 5.0 | 5.5 | 4.0 | 5.0 | 6.0 | 4.0 |
| 'Tifdwarf' | 5.0 | 4.0 | 4.5 | 4.0 | 5.0 | 3.5 |
| 'Champion' | 4.0 | 3.0 | 4.0 | 4.0 | 5.0 | 4.0 |
| LSD(0.05) | 0.9 | 1.8 | 1.8 | 0.9 | 0.9 | 1.6 |

Inflorescence and Other Characteristics

Figure 4:
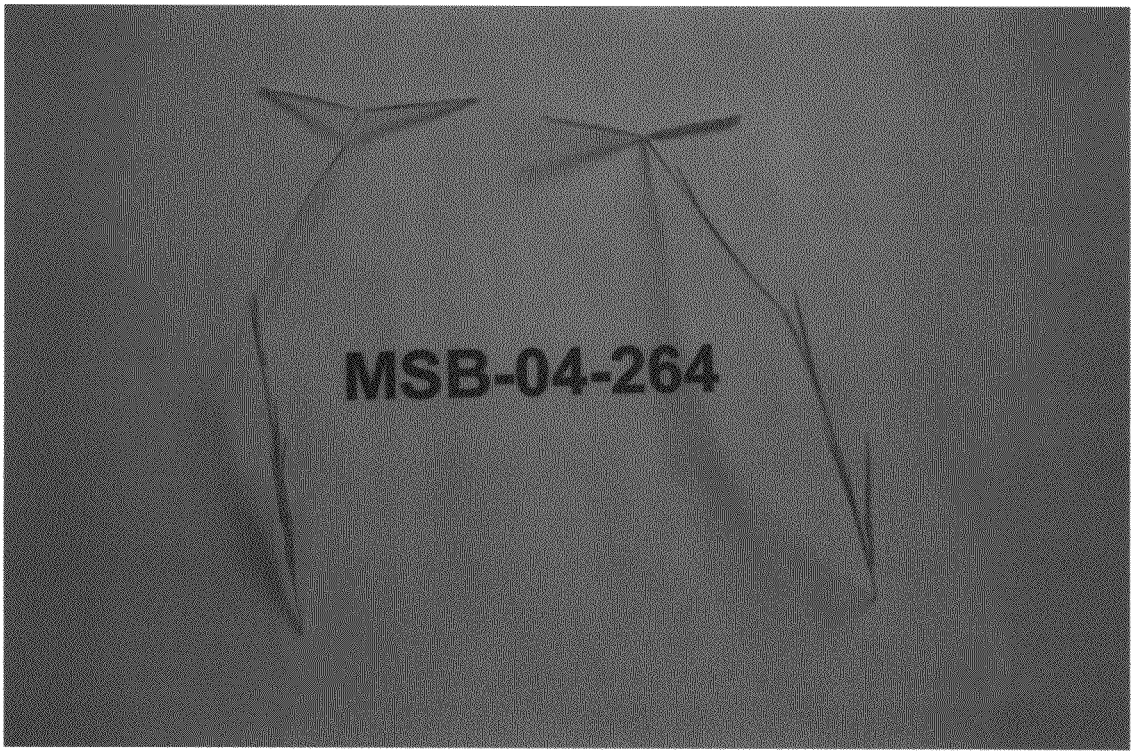
FIG. 4 is a photograph of the inflorescence of the new cultivar 'MSB-04-264'.

The inflorescence of 'MSB-04-264' is a digitate spike with two finger-like branches that attach to the main rachis at a central point (FIG. 4). Inflorescences of 'MSB-04-264' were measured on greenhouse-grown unmowed pots. The mean peduncle length is 35.9 mm and the mean branch length is 16.8 mm. The number of branches per inflorescence of 'MSB-04-264' and 'Tifdwarf' bermudagrass was determined from field plots that had been maintained at 0.125-inch mowing height, then left unmowed for two weeks. Forty (40) inflorescences were observed for each cultivar. All inflorescences (100%) of 'MSB-04-264' contained two branches. 'Tifdwarf' displayed 19 of 40 inflorescences (47.5%) having three branches and 21 of 40 inflorescences (52.5%) having two branches. The stigmas of 'MSB-04-264' are purple and the anthers are yellow. Like other interspecific triploid hybrid bermudagrasses, 'MSB-04-264' produces no viable pollen. No seed production has been observed.

The leaf blade color of 'MSB-04-264' is dark green and is rated 7.5 GY 4/4 based on the Munsell® Color Chart for plant tissue. The color determination was conducted in March, 2011 on unmowed pots grown in a greenhouse under natural sunlight conditions. Vernation is folded. The ligule is a fringe of hairs.

'MSB-04-264' has not yet been screened for resistance or susceptibility to various turf diseases. During nine years of evaluating this new grass at test sites in Mississippi, the inventors have occasionally observed symptoms of leaf spot disease caused by *Bipolaris cynodontis*. From this, the inventors have concluded that 'MSB-04-264' is at least moderately susceptible to this disease. On one occasion when symptoms were present, this new cultivar was sprayed with a systemic strobilurin type of fungicide. The disease symptoms soon disappeared with no lasting effect.

Most bermudagrass cultivars are susceptible to dollar spot disease caused by *Sclerotinia homoecarpa*. While cultivars in surrounding plots have displayed symptoms, no dollar spot disease has been observed on 'MSB-04-264' in Mississippi. While the inventors cannot assume that 'MSB-04-264' is resistant to dollar spot disease, it is unlikely that the new bermudagrass plant is highly susceptible to this disease.

Regarding insect resistance/susceptibility, the inventors have observed no insect damage on the new grass cultivar 'MSB-04-264' in the nine years it has been researched in Mississippi.

Stolon Morphology

The stolon morphology of bermudagrass cultivars was measured on greenhouse-grown pots near Starkville, Miss. in 2010. Four (4) six-inch-diameter pots were established from each of seven cultivars (Table 6). The pots were frequently clipped until all had achieved full turf density, then allowed to grow unmowed for six weeks prior to measurement. Forty-five (45) randomly-selected leaf blades from each cultivar were measured for length and width. Stolons that grew off each pot were used to measure the relative stolon length, internode diameter, and internode length. Unmowed plant height was measured at the center of each pot and represents the distance from the soil line to the tips of the uppermost leaves in the canopy.

Leaves of 'MSB-04-264' were found to be significantly longer and narrower than the commercial cultivars 'Champion', 'TifEagle', and 'Tifdwarf'. The internode length of 'MSB-04-264' was found to be shorter than 'Champion' and slightly but not significantly longer than 'Tifdwarf' and 'TifEagle'. The internode diameter of 'MSB-04-264' was significantly larger than 'Champion', 'TifEagle', and 'Tifdwarf'. The stolon length of 'MSB-04-264' was slightly longer than 'Tifdwarf' and significantly longer than 'TifEagle' and 'Champion'. The unmowed plant height of 'MSB-04-264' was significantly taller than 'Tifdwarf', 'TifEagle', and 'Champion'.

TABLE 6

Stolon morphology of bermudagrass cultivars grown in a greenhouse in unmowed pots near Starkville, MS in 2010.

| Cultivar | Leaf Blade Length mm | Leaf Blade Width mm | Inter-node Length mm | Internode Diameter mm | Stolon Length cm | Unmowed plant height cm |
|---|---|---|---|---|---|---|
| 'MSB-04-264' | 32.9 | 1.18 | 24.0 | 0.84 | 14.9 | 5.9 |
| 'MSB-04-265' | 31.6 | 1.31 | 23.6 | 0.85 | 12.2 | 5.5 |
| 'MSB-05-268' | 43.8 | 1.47 | 34.3 | 0.90 | 17.1 | 8.5 |
| 'MSB-05-271' | 38.8 | 1.42 | 29.5 | 0.94 | 13.2 | 4.8 |
| 'Champion' | 16.0 | 1.43 | 26.1 | 0.72 | 9.0 | 3.0 |
| 'TifEagle' | 27.0 | 1.50 | 23.8 | 0.78 | 10.8 | 4.8 |
| 'Tifdwarf' | 29.4 | 1.46 | 23.0 | 0.71 | 12.4 | 4.6 |
| LSD (0.05) | 3.4 | 0.08 | 1.6 | 0.04 | 2.8 | 1.0 |

Leaf Orientation

An experiment was conducted in 2010 to compare the leaf orientation (upright vs. prostrate) of bermudagrass cultivars by counting the number of leaves clipped by mowing. Small plots were established at four putting green sites including a research center and one golf course in Oktibbeha County, Miss. and two golf courses in Lowndes County, Miss. The plots were arranged in a randomized complete block design with three replications. The sites were mowed daily at a 0.125-inch height with reel mowers designed for golf putting greens. After at least one month of mowing, a 5-cm diameter ring was randomly dropped onto each plot and digitally photographed. From the digital images, the clipped leaves inside each sample area were counted (Tables 7, 8, and 9). At all four sites, 'MSB-04-264' displayed significantly more clipped leaf blades than the other cultivars, including 'Tifdwarf', 'TifEagle', 'Champion', and 'Mini-Verde' (See also FIGS. 1A and 1B). This verifies that the leaf orientation of 'MSB-04-264' is more upright than the ultradwarf cultivars presently being used on golf course putting greens.

TABLE 7

Number of clipped leaves per 5-cm diameter sample of bermudagrass cultivars grown at a plant science research center at Starkville, MS in 2010.

| Cultivar | July 21 | October 14 | Mean |
|---|---|---|---|
| 'MSB-04-264' | 80.3 | 54.3 | 64.7 |
| 'TifEagle' | 50.3 | 28.3 | 37.1 |
| 'Tifdwarf' | 45.0 | 27.0 | 34.2 |
| 'Champion' | 38.0 | 23.3 | 29.2 |
| LSD(0.05) | 24.3 | 9.2 | 10.2 |

TABLE 8

Number of clipped leaves per 5-cm diameter sample of bermudagrass cultivars grown at a university golf course at Starkville, MS in 2010.

| Cultivar | July 30 | August 6 | August 20 | October 7 | Mean |
|---|---|---|---|---|---|
| 'MSB-04-264' | 25.3 | 44.7 | 47.7 | 43.7 | 40.3 |
| 'TifEagle' | 8.7 | 29.7 | 11.3 | 21.7 | 17.8 |
| 'Tifdwarf' | 5.0 | 5.7 | 14.7 | 30.0 | 13.8 |
| 'Champion' | 7.0 | 4.3 | 14.0 | 19.7 | 11.6 |
| 'Mini-Verde' | 9.0 | 5.3 | 7.0 | 22.0 | 10.8 |
| LSD(0.05) | 12.9 | 7.6 | 21.7 | 20.4 | 7.8 |

TABLE 9

Number of clipped leaves per 5-cm-diameter sample of bermudagrass cultivars at Columbus, MS in 2010.

| Cultivar | Golf Course No. 1 September 2 | Golf Course No. 2 September 2 |
|---|---|---|
| 'MSB-04-264' | 56.0 | 22.3 |
| 'TifEagle' | 27.7 | 9.3 |
| 'Tifdwarf' | 23.0 | 8.0 |
| 'Champion' | 23.0 | 6.5 |

TABLE 9-continued

Number of clipped leaves per 5-cm-diameter sample of bermudagrass cultivars at Columbus, MS in 2010.

| Cultivar | Golf Course No. 1 September 2 | Golf Course No. 2 September 2 |
|---|---|---|
| 'Mini-Verde' | 23.7 | 5.0 |
| LSD(0.05) | 32.0 | 9.1 |

What is claimed is:

1. A new and distinct variety of Bermudagrass plant, substantially as herein illustrated and described.

* * * * *